(12) United States Patent
Delcourt et al.

(10) Patent No.: US 7,202,086 B2
(45) Date of Patent: Apr. 10, 2007

(54) METHOD FOR MASSIVE DIRECTED MUTAGENESIS

(75) Inventors: Marc Delcourt, Villejuif (FR); Stephane Blesa, Roissy-en-Brie (FR)

(73) Assignee: Biomethodes, Evry (FR)

( * ) Notice: Subject to any disclaimer, the term of this patent is extended or adjusted under 35 U.S.C. 154(b) by 370 days.

(21) Appl. No.: 10/362,576

(22) PCT Filed: Aug. 24, 2001

(86) PCT No.: PCT/FR01/02666

§ 371 (c)(1),
(2), (4) Date: Aug. 6, 2003

(87) PCT Pub. No.: WO02/16606

PCT Pub. Date: Feb. 28, 2002

(65) Prior Publication Data

US 2004/0048268 A1    Mar. 11, 2004

(30) Foreign Application Priority Data

Aug. 25, 2000   (FR)   .................................. 00 10962

(51) Int. Cl.
*C12N 1/15* (2006.01)
*C12Q 1/68* (2006.01)
*C07H 21/02* (2006.01)
*C07H 21/04* (2006.01)

(52) U.S. Cl. .................. 435/440; 435/6; 536/23.1; 536/24.3

(58) Field of Classification Search ............... 435/6, 435/440; 536/23.1, 24.3
See application file for complete search history.

(56) References Cited

U.S. PATENT DOCUMENTS

| 4,960,707 A | * | 10/1990 | Lacks | ....................... 435/320.1 |
| 5,605,793 A | * | 2/1997 | Stemmer | ....................... 435/6 |
| 5,798,208 A | | 8/1998 | Crea | |
| 5,811,238 A | * | 9/1998 | Stemmer et al. | ................ 435/6 |
| 5,830,696 A | * | 11/1998 | Short | ........................ 435/69.1 |
| 6,368,861 B1 | * | 4/2002 | Crameri et al. | ............. 435/440 |

OTHER PUBLICATIONS

Wells et al. "Cassette mutagenesis: an efficient method for generation of multiple mutations at defined sites" Gene 34 : 315-323(1985).*

Grundstrom et al. "Oligonucieotide-directed mutagenesis by microscale 'shot-gun' gene synthesis" Nuclic Acids Research 13: 3305-3316 (1985).*

Stemmer, W.P. Rapid Evolution of a protein in vitro by DNA shuffling. Nature 370 : 389-391 (Aug. 1994).*

Perlak, F.J. Single step large scale site-directed in vitro mutagenesis using multiple oligonucleotides. Nucleic Acids Research 18(24) : 7457-7458 (1990).*

Picard et al. A rapid and efficient one-tube PCR-based mutagenesis technique using Pfu DNA polymerase. Nucleic Acids Resaearch 22(13) : 2587-2591 (1994).*

New England Biolabs Catalog, p. 70 (1995).*

Xiao et al Science in China, Series C: Life Sciences, vol. 40, No. 4, 1997, pp. 337-344, XP000993443 "Construction and screening of a multi-point site-specific mutant library of subtilisin E with a set of oligonucleotides".

* cited by examiner

*Primary Examiner*—Ethan Whisenant
(74) *Attorney, Agent, or Firm*—Nixon & Vanderhye P.C.

(57) ABSTRACT

The invention concerns the field of molecular biology and more particularly that of mutagenesis. It concerns a method of high-rate directed mutagenesis, that is the formation of numerous directed mutants in reduced time and with reduced number of steps. Said method is therefore referred to as massive mutagenesis.

27 Claims, 5 Drawing Sheets

Fig.2 (follow)

Fig.3

XXXXXXX    PGTXXXXXXX
XXXXXXXCA    XXXXXXX

Ligation with T4 Ligase

XXXXXXXGTXXXXXXXX
XXXXXXXCA XXXXXXX

Fig.4

CCGTGTGATNACGTGCAGA    4 molecular species

ATCGATAGGNNAGAGTCTTA    16 molecular species

ATGGGATGANNNAGTTCGATG    64 molecular species

METHOD FOR MASSIVE DIRECTED MUTAGENESIS

The present application is a 371 U.S. national phase of PCT/FR01/02666, filed 24 Aug. 2001, which designated the U.S., the entire contents of which is incorporated herewith by reference.

The present invention relates to the field of molecular biology and more particularly mutagenesis. It concerns a method for high-throughput directed mutagenesis, i.e. the formation of a great number of directed mutants within a limited time and in a limited number of stages. This method will therefore be referred to "massive mutagenesis".

Mutagenesis is a technique aiming at artificially modifying the nucleotide sequence of a DNA fragment in order to modify the biological activity deriving from it. In the last decade mutagenesis has taken up an important position in numerous molecular biology studies.

The term mutagenesis can be associated with three distinct modifications of a DNA fragment:
 deletion, which consists in eliminating nucleotides from the DNA fragment of interest,
 insertion, which consists in adding nucleotides, and
 substitution, which consists in replacing one or more bases with the same number of bases of a different type.

Mutagenesis techniques can be classified into two main groups: random mutagenesis and directed mutagenesis.

The purpose of random mutagenesis is to introduce substitutions of random nature and position into a DNA fragment. Random mutagenesis was formerly carried out by means of chemical processes, which alter the DNA structure. More recently, amplification of a molecule using a polymerase in particular conditions has often replaced chemical processes. These particular conditions are characterised in that they alter the capacity of the enzyme to replicate the DNA accurately. In the course of the cycles, the enzyme introduces mutations, i.e. differences from the initial sequence. At the end of the reaction, a large number of copies of the initial molecule are obtained, each of these molecules having different mutations. These molecules are present as a library, i.e. a mixture of molecules of different types (differing in the nature and position of their mutations).

The purpose of directed mutagenesis is to introduce one or more mutations (substitutions, but also deletions or insertions) of known nature and position into a DNA fragment. An oligonucleotide is used to introduce this mutation. This oligonucleotide usually comprises about 20 bases. The sequence of this oligonucleotide is homologous to the sequence of the target DNA fragment everywhere but in one or more positions located in its median part.

This oligonucleotide is then used as a primer in a replication reaction (or amplification reaction, i.e. multiple replications) using the DNA fragment as the template. The newly synthesised sequence contains the desired modification.

The first techniques of directed mutagenesis were based on amplification of the DNA fragment of interest (only as of a fragment of linear DNA), which then had to be introduced into a plasmid. These techniques were tedious and had to be adapted to each studied system.

More recently, the mutant oligonucleotide has been used to replicate directly the plasmid containing the DNA fragment of interest. Thus the number of operations to be carried out is reduced.

However the practical implementation of directed mutagenesis is far from simple. Especially there arises the problem of isolating the molecules, which incorporated the mutation from the molecules, which did not incorporate it. Simple replication of a fragment of circular DNA (corresponding to the conventional case of a gene cloned in a plasmid) by means of a mutant oligonucleotide does not make it possible to observe a detectable level of mutagenesis, in the absence of a selection system. In vitro synthesised DNA can be distinguished from DNA synthesised in bacteria on the basis of its methylated base content, and a screening system based there on has been developed and come into general use. This involves the use of the enzyme DpnI, which is specific for sites present on methylated DNA, but not on non-methylated DNA (Lacks et al., 1980, Methods in Enzymology, 65:138). The molecules which have not been replicated in vitro are thus eliminated. However even by using this mutant screening system, the efficiency of the mutagenesis reaction remains low and close to 5% of mutant molecules only.

This low level of mutants is notably due to the fact that at the end of the directed mutagenesis reaction, the circular molecules are introduced into bacteria containing a DNA repair system which eliminates a large number of the mutations if they are carried by only one of the DNA strands.

Many systems have been proposed to attempt to improve the efficiency of these mutagenesis techniques. Such systems usually involve a second oligonucleotide which makes it possible to improve the frequency of mutant molecules before screening (Patent EP 96942905; Patent WO 9935281). Other systems also use a second nucleotide allowing a particular and sometimes more effective system of screening (Patent EP 0938552, Clontech Catalogue 2000, page 45). Finally, other systems involve particular bacterial strains and the purpose of these systems is to minimize the loss of yield due to the repairing activity of the bacteria (U.S. Pat. No. 4,873,192; Patent EP 0938552).

Finally, most of the existing techniques make it possible to incorporate several oligonucleotides into a DNA sequence simultaneously. It has generally been possible to simultaneously introduce up to 3 oligonucleotides in different parts of the fragment to be mutated (Patent WO 9935281; Patent EP 0938552). It has even been reported that molecules having simultaneously incorporated up to 7 oligonucleotides could be obtained in a one-step process (Perlak et al. 1990, Nucleic Acid Research, 18: 7457).

According to the prior art, the concept of a library is not appropriate to characterize the products obtained by a directed mutagenesis. In most cases, what is obtained at the end of the reaction is a single product containing a single mutation. When several mutations are simultaneously introduced by means of several nucleotides (Patent WO 9935281; Perlak et al., 1990, Nucleic Acid Research, 18: 7457), the only desired products are those which have incorporated all the mutations, and the technique tends to be optimized in order to maximize the frequency of these products. Products which have incorporated a small fraction only of the mutations are minimized and they are considered as secondary products in these reports.

The purpose of mutagenesis may be gain or loss of activity.

Gain of an activity, or more frequently a mere improvement thereof, is especially interesting in the field of enzymology and ligand/receptor combination. Thus providing enzymes with improved activity could make it possible to reduce the costs of industrial processes using such enzymes. In the same way, the affinity of the bond between a ligand and its receptor can be improved by means of a few mutations located at the recognition site.

The search for these improvements in activity is often described generically as "molecular evolution". This means simulating evolution in in vitro reactions by introducing mutations into a DNA fragment and selecting those with improved activities. Several cycles of mutagenesis/selection thus mimic the evolution of a molecule in the presence of a selection pressure.

Most often used in this context is random mutagenesis. As a matter of fact, since there is generally no element which makes it possible to define a priori the nature and position of the changes likely to bring about an improvement in the activity of interest, it is necessary to produce a large number of molecules each having mutations of different position and nature, in order to maximize the chances that a molecule corresponding to improved activity will be found among them.

The loss of biological activity associated with a DNA fragment which has been subjected to mutagenesis provides particular information on the amino acids supporting this activity. Thus, if change of an amino acid results in loss of biological activity, probably this amino acid is involved in the formation of the active site supporting this biological activity. However, these results should be considered very cautiously: for example, this amino acid may not be involved directly in the active site of the biological activity and just contribute in associated activities, such as the intracellular addressing of the protein. On the other hand, the modification introduced may destabilise the whole protein, in which case the effect of the substitution introduced is indirect and not direct. For these two reasons, it is important to be able to recognize on a gene coding for a protein the moieties which support the activities of addressing, membrane localisation, co-factor binding . . . Further it is essential that the modifications introduced leads to a minimal destabilisation of the protein. Most often small hydrophobic amino acids, such as alanine or valine, are introduced in lieu of the original amino acids. These small amino acids are known to retain the majority of the secondary protein structures (_-helix or _-sheet), and therefore to minimize the overall destabilisation of the proteins.

The work carried out in this field involves the creation of a large number of point mutants each having substitution of a different amino acid of the protein by an alanine. This necessitates a huge amount of work as each mutant has to be made independently.

There are exceptions to the general cases presented above. Directed mutagenesis has been used in the context of a search for a gain in activity. When the region of the active site is well known, it may be expected that directed modification of those amino acids which constitute it leads to improved activity. Thus European Patent No. 527 809 discloses sequentially replacing the amino acids in an active region with an amino acid frequently involved in active sites (for example serine) using a technique similar to directed mutagenesis. However, this technique requires that precise information about the active site of the molecule of interest is available, and uses a technology which does not allow the introduction of a large number of modifications on a DNA fragment.

Conversely random mutagenesis experiments have been carried out in a search for loss of activity (Loeb et al. 1989, Nature, 340: 397). In this case, a very large number of clones have to be analysed in order to obtain consistent results and thus get free from the limitation of random replacement.

The present invention is an intermediate technique between directed mutagenesis and random mutagenesis. It does not aim, as it is the case in simple directed mutagenesis, at obtaining at the end of the reaction a single product containing the desired mutation or mutations, but a mixture of molecules each containing one or more of the desired mutations. The present invention is a method for introducing a particular predefined type of substitution at a given position, rather than any substitution, as it is the case in random mutagenesis.

Thus this method combines the advantages of directed mutagenesis (control of the nature of the modifications obtained in a given position) and of random mutagenesis (achievement of a large number of different mutations distributed over many positions in the DNA fragment to be mutated). It makes it possible to carry out a large number of directed mutations within a very short time.

These objectives are achieved according to the invention by a process of mutagenesis of a target gene, which comprises preparing a pool of N oligonucleotides with a sequence substantially complementary to at least one region of the target gene, then reacting said pool of oligonucleotides with said target gene under conditions which allow production of copies of the target gene carrying at least one mutation. The target gene is carried by a double-strand circular plasmid. Each oligonucleotide has a sequence complementary to a different region of the target gene, with at least one mutation in the centre of the oligonucleotide sequence. The whole of said N oligonucleotides of the pool, with N higher than 5, encompasses part or all of the sequence of said target gene. Said pool of oligonucleotides is then reacted with the target gene in the presence of a polymerase in order to generate a library of mutated genes where each mutation from a single oligonucleotide is present in less than $\frac{1}{5}$ of the genes in the library on average.

The process according to the invention is remarkable in that the limitations associated with the position of the mutation and its nature are dissociated; for example, it is possible to carry out mutations of a particular type (for example any codon to alanine) throughout a coding sequence. In this example, each of the mutants obtained at the end of the reaction contains one or more mutations of known nature (alanine codon) but of unknown position. Alternatively, the process of the invention makes it possible to incorporate in some particular positions oligonucleotides containing degenerated bases. In this example, the positions are somewhat known (the number of positions is limited), but the nature of the mutations introduced is unknown.

These characteristics contrast with the random mutagenesis techniques where neither the nature nor the position of the mutations are known, and conventional directed mutagenesis techniques where both nature and position of the mutation introduced are known.

Another remarkable feature of the process according to the invention consists in that the mutagenesis reaction, results in the final production of a large number of different molecules of DNA, which form a library. These molecules correspond to all the DNA molecules which have incorporated at least one mutation at predetermined sites. The number of different mutant molecules is very high because all the combinations of mutations can occur.

The process of mutagenesis according to the invention can also be applied to a library of mutated genes. This library is then used as a template instead of the target gene. A pool of N oligonucleotides with a sequence substantially complementary to at least one region of the target mutated genes is prepared and said oligdnucleotides pool is then reacted with the target mutated genes under conditions which allow the production of copies of the target mutated genes carrying at least one mutation. The target mutated genes are carried by double-strand circular plasmids and each oligonucleotide has a sequence complementary to a different region of the target mutated genes with at least one mutation in the centre of the oligonucleotide sequence, and the whole of the said N oligonucleotides of the pool, with N higher than 5, encompasses part or all of the sequence of said target mutated genes. Said pool of oligonucleotides is then reacted with the target mutated genes in the presence of a polymerase in order to generate a library of mutated genes where each mutation from a single oligonucleotide is present in less than 1/5 of the genes in the library on average.

In another application of the process according to the invention, the library of target mutated genes used as the template has been first obtained by massive mutagenesis. The average number of mutations per molecule increases with the number of cycles of massive mutagenesis carried out.

According to an advantageous embodiment of the process of the invention, N is between about 5 and $10^6$, preferably between 50 and 500, and each mutation from a single oligonucleotide is present in 1/5 to $1/10^6$, preferably in 1/50 to 1/500 of the genes in the library on average.

The process of the invention is especially directed to the case where the pool of oligonucleotides comprises N different oligonucleotides and where each mutation from a single oligonucleotide is present in about 1/N of the genes in the library on average, with N having the above value.

This feature distinguishes the process of the invention from the prior art, where the examples of multiple mutagenesis using several oligonucleotides simultaneously are based on levels of incorporation of each oligonucleotide of more than 75%. The purpose of these approaches is to isolate the only mutants which have incorporated all the oligonucleotides, and the high levels of incorporation make it possible to achieve this easily. By contrast, in the process according to the invention, the frequency of mutation for each of the mutations to be introduced is controlled in order to avoid the production of DNA molecules containing an excess of mutations. It is desired to get mutants each containing one mutation or a combination of some different mutations. In order to achieve this end, the ratio between the quantity of each mutant oligonucleotide and the quantity of template to be mutated must be controlled. This ratio is between 0.01 and 100, preferably between 0.1 and 10.

The reaction of the pool of oligonucleotides with the target gene or with the library of target mutated genes can be carried out using different types of polymerase, preferably heat-stable polymerases. A first embodiment uses a polymerase with a strand displacement activity such as Taq polymerase, or an exonuclease 3'→5' activity such as Pfu polymerase. In this embodiment the reaction can take place in the presence of a ligase. A second embodiment uses a polymerase with no strand displacement or exonuclease 3'→5' activity such as T4 polymerase, and in this case the reaction is carried out in the absence of a ligase.

The oligonucleotides in the pool have a size between 10 and 100 and preferably between 15 and 25 nucleotides. Each of them is homologous to a part of the DNA sequence to be mutated, with the exclusion of one or several positions located in its inner part, which constitute the mutation or mutations to be introduced. These oligonucleotides can be overlapping, i.e. comprise sequences common to two different adjacent regions. Preferably, all the oligonucleotides have the same orientation, so that only one strand of the target gene is replicated, which makes it possible to obtain a low level of mutagenesis.

In a particular embodiment the oligonucleotides are reconstructed from two oligonucleotides, according to the process described in U.S. Pat. No. 5,858,731.

Advantageously each oligonucleotide comprises one or more mutations and preferably one to three mutations placed at the centre of its sequence.

Said mutations of each oligonucleotide can be chosen from among the deletions and/or insertions of one or more nucleotides.

A particular form of mutation comprises using degenerated oligonucleotides. This means that each oligonucleotide in the pool is present in several copies, each of these copies having a different nucleotide at the site of said mutation or mutations.

In another particular form of mutation, each mutation allows to introduce into each oligonucleotide an identical codon or a codon corresponding to the same amino acid, as substituted for the original codon of the target gene. Advantageously, said codon corresponds to an amino acid chosen from the group Ala, Val, Gly, Leu, Ile.

The process according to the invention can be described more specifically, as including the following steps:

A template is prepared, preferably a plasmid containing the DNA fragment or fragments to be mutated.

Different mutant oligonucleotides, preferably between 5 and $10^6$ and more preferably between 50 and 500, are synthesised, followed by combining all the mutant oligonucleotides. In this step, concentration of each oligonucleotide in the mixture is thus divided by the number of oligonucleotides.

The oligonucleotides are added to the template, i.e. to the plasmid containing the DNA fragment or fragments to be mutated, at a concentration such that the ratio between the number of template molecules and the number of molecules of each mutant oligonucleotide is between 0.01 and 100, preferably between 0.1 and 10.

The template is denatured by heat (about 95° C.) so that some single-strand DNA is available for a while. When cooling back to low temperature, some or all of the oligonucleotides present in the mixture bind to the template at their site of homology.

All the elements necessary to carry out replication of the template from the mutant oligonucleotides, i.e. a polymerase, a buffer allowing it to be effective, triphosphate nucleotides in sufficient amount and any necessary co-factors, are added. Then the replication reaction takes place under temperature conditions corresponding to the maximum activity of the polymerase. If appropriate, a ligase can be added during the replication stage so that the newly synthesized DNA strands bind to the 5' end of another oligonucleotide, bound to the template at 3' of the first oligonucleotide. In this case, the oligonucleotides are previously phosphorylated.

The denaturation and replication stages are optionally repeated several times. In this case, preferably, the polymerase is heat-stable to avoid the need to add some more enzyme during each cycle. At the end of the reaction, the DNA molecules present in the mixture are of several types:

Initial double-strand template which has not been effectively replicated; and

Some molecules which have been replicated, i.e. they contain one original strand and one strand newly synthesised from one or more primers comprised by the mutant oligonucleotides.

The mixture obtained is subjected to digestion by the DpnI enzyme or another restriction enzyme which allows to suppress the methylated DNA molecules on the two strands and to maintain those which are not methylated or semi-methylated.

Competent bacteria are transformed with the above mixture and then spread on a medium containing a selective agent in order to select those bacteria which have integrated a plasmid. The DNA molecules which were cleaved in the previous stage are eliminated because the presence of a complete circular plasmid is essential to survival of the bacteria in the selective medium.

The bacterial colonies obtained are sampled individually and used to inoculate a selective nutrient medium. A plasmid DNA preparation of these cultures is then carried out in order to isolate a large amount of potentially mutant plasmid DNA. Examination of the various plasmid DNA molecules at this stage allows to calculate the mean level of incorporation of each oligonucleotide and to check that it is close to the required value.

Optionally the biological activity corresponding to the various batches of mutant plasmid preparations is tested. The activity measured can be higher, equal or lower than that of the non-mutated fragments. If the activity is changed, the corresponding plasmid is sequenced in order to locate the mutation introduced. In a preferred embodiment the biological activity of the mutant molecules is tested and the result is compared with the biological activity corresponding to the non-mutated plasmid DNA molecule. If these measurements show a significant difference, the mutant molecules are sequenced in order to detect the position of the mutation which induces this change of activity. The order of these last two stages is opposite to that in conventional directed mutagenesis techniques, which generally involve obtaining and checking the mutant molecule before testing its biological activity.

Thus an embodiment of the mutagenesis process according to the invention comprises the following steps:
a) a template is prepared consisting of a plasmid containing the target gene or the library of target mutated genes and a resistance gene,
b) an equimolar pool of oligonucleotides with a sequence complementary to a different region of the target gene or the library of target mutated genes and at least one mutation at the centre of the oligonucleotide is prepared, so that the set of oligonucleotides encompasses all or part of the sequence of said target gene or genes,
c) the pool of oligonucleotides prepared in step (b) is mixed with the plasmid from step (a) in a molar ratio of each oligonucleotide to the plasmid between 0.01 and 100 and preferably between 0.1 and 10,
d) the mixture from step (c) is denatured by raising temperature to give a single-strand template,
e) the mixture from step (d) is subjected to a temperature allowing hybridisation of oligonucleotides on the template,
f) at least one polymerase, its buffer and its co-factors and a sufficient amount of each of the triphosphate nucleotides to allow replication of the strands of the template from any of the oligonucleotides are added to the mixture,
g) optionally, steps (d), (e) and (f) are repeated,
h) the products of step (f) or (g) which have undergone replication are selected by any appropriate means,
i) competent bacteria are transformed with the products selected in step (h) and those products with a plasmid are selected on a selective medium corresponding to the resistance gene carried by the plasmid from step (a).

Advantageously in the above step (h), the products from step (f) are subjected to the action of a restriction enzyme which is specific to the products which have undergone replication, such as the DpnI enzyme.

The oligonucleotides can be phosphorylated at their 5' end when a ligase is added in step (f), advantageously a heat-stable ligase.

The mutagenesis process according to the invention is particularly useful for measuring the biological activity of the mutated proteins encoded by the mutated target genes. Consequently the target gene is a nucleic acid molecule coding for a protein of interest with or without its own regulation sequences. If the target gene does not include regulation sequences such as a promoter, the sequences are present in the plasmid.

The invention also relates to a process of mutagenesis of a target protein or a library of target mutated proteins, characterized by comprising preparation of an expression library of genes mutated from a target gene coding for said protein according to the mutagenesis process described above, expression of said mutated genes to produce a library of mutated proteins, and optionally screening of said mutated proteins for a desired function, advantageously in relation to the target protein.

The invention thus makes it possible to carry out a process of selection of mutated proteins having modified activity compared with the same non-mutated protein, or of the mutated genes corresponding to said mutated proteins, comprising the mutagenesis process as described above, screening of said mutated proteins for a desired function, advantageously in relation to the target protein, selection of the mutated protein having the desired function, and optionally sequencing of the mutated gene corresponding to said mutated protein.

These processes for mutagenesis of a target protein or a library of target mutated proteins or selection of a mutated protein or the corresponding gene according to the invention are characterized in that they include the preparation of an expression library comprising genes mutated from a target gene coding for said protein, and then the following steps:
j) the selective medium is incubated at an appropriate temperature for a time sufficient for growth of individual bacterial colonies,
i) individual cultures of bacteria from colonies in step (i) are inoculated;
l) preparations of plasmid DNA are made from the cultures from step (k),
m) the biological activity associated with each plasmid DNA preparation from step (l) is measured and the result obtained is compared with that measured using non-mutated plasmid DNA,
n) optionally, the plasmid DNA preparations which show significant modifications of biological activity are sequenced.

Any further object of the invention is a pool of oligonucleotides mutated in relation to a target gene or the library of target mutated genes as defined above.

Still a further object of the invention is a library of mutated genes which can be obtained by the process described above, characterized in that each different mutation is present on average in less than 1/5 of the genes in the library and preferably on average in about 1/N of the genes in the library, where N is higher than 5, preferably between 5 and $10^6$ and more preferably between 50 and 500. Preferably this library is obtained, in accordance with the invention process, by using N oligonucleotides with N higher than 5, preferably between 5 and $10^6$ and more preferably between 50 and 500.

Other advantages and characteristics of the invention will be apparent from the following non-limiting examples, and the attached drawings in which:

FIG. 1 represents a distribution of the mutant oligonucleotides on the sequence of the CD4 molecule. Each of the oligonucleotides contains 3 mutations at most, represented by the break of the arrow line, located in its centre, intended to change said codon into alanine. The oligonucleotides overlap each other and are represented on 3 levels for sake of clarity. In the example in FIG. 1, only 24 mutant oligonucleotides are represented. In example 1 below, 95 oligonucleotides were used simultaneously. In this example all the oligonucleotides carrying the mutations have the same orientation.

(a) polymerisation (polymerase, dNTP, buffer and co-factors);
(b) digestion by DpnI to eliminate the initial matrices;
(c) transformation of competent bacteria and spreading on selective medium;
(d) inoculation of bacterial cultures from the colonies isolated and preparation of plasmid DNA;
(e) phenotype test, then selection and sequencing of the mutants with the required phenotype.

EXAMPLE 1

Alanine Scanning

A gene coding for the molecule CD4 was introduced into the vector SK+. The first 95 codons of this gene were the target of a massive mutagenesis reaction according to the invention process.

Figure 1:
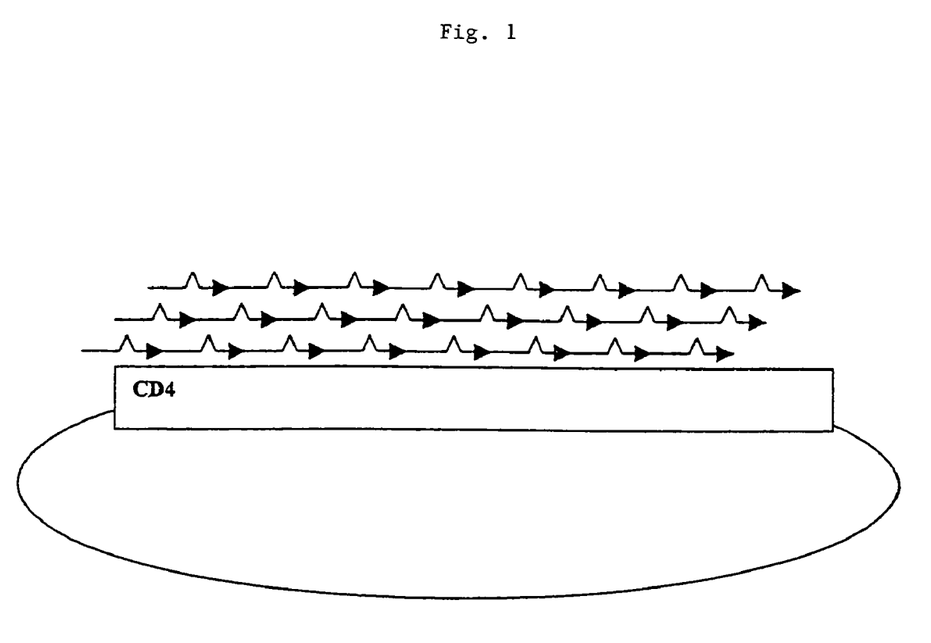

A pool of 95 oligonucleotides of 21 bases were synthesized. Each of these oligonucleotides was complementary to a sequence of the CD4 gene centred on a codon. For example, the first oligonucleotide was homologous to a sequence centred at codon 1. It was homologous to the sequence of 9 bases on each side of said codon, but it contained 3 mutations, in order to convert the first codon into an alanine codon (FIG. 1).

In the same way, the second oligonucleotide was centred at the second codon and contained 3 adjacent mutations in its middle.

The 95 oligonucleotides, which overlapped each other and were all in the same orientation, were then mixed in equimolar amount and phosphorylated using the T4 kinase in standard conditions.

| The following mixture was then prepared: | |
|---|---:|
| SK-CD4 template (250 µg/µl): | 1 µl |
| MIX of the 95 nucleotides 5'P (0.5 µM each) | 2 µl |
| dNTP triphosphates (2.5 mM) | 10 µl |
| 10X of Pfu polymerase buffer | 2.5 µl |
| ATP 10 mM | 0.5 µl |
| Pfu polymerase (2.5 U/µl) | 1 µl |
| Pfu ligase (4 U/µl) | 1 µl |
| H$_2$O | 7 µl |
| Total | 25 µl |

The mixture was subjected to reaction during 12 temperature cycles [(94° C., 1'); (35° C., 1'); (68° C., 20')].

The reaction mixture was then subjected to digestion by 5 units of DpnI enzyme in appropriate buffer, for 30 minutes at 37° C.

Competent bacteria were converted by this mixture using a thermal shock protocol and spread on a Petri dish containing the appropriate selective agent.

The next day a thousand bacteria were obtained.

Figure 2:
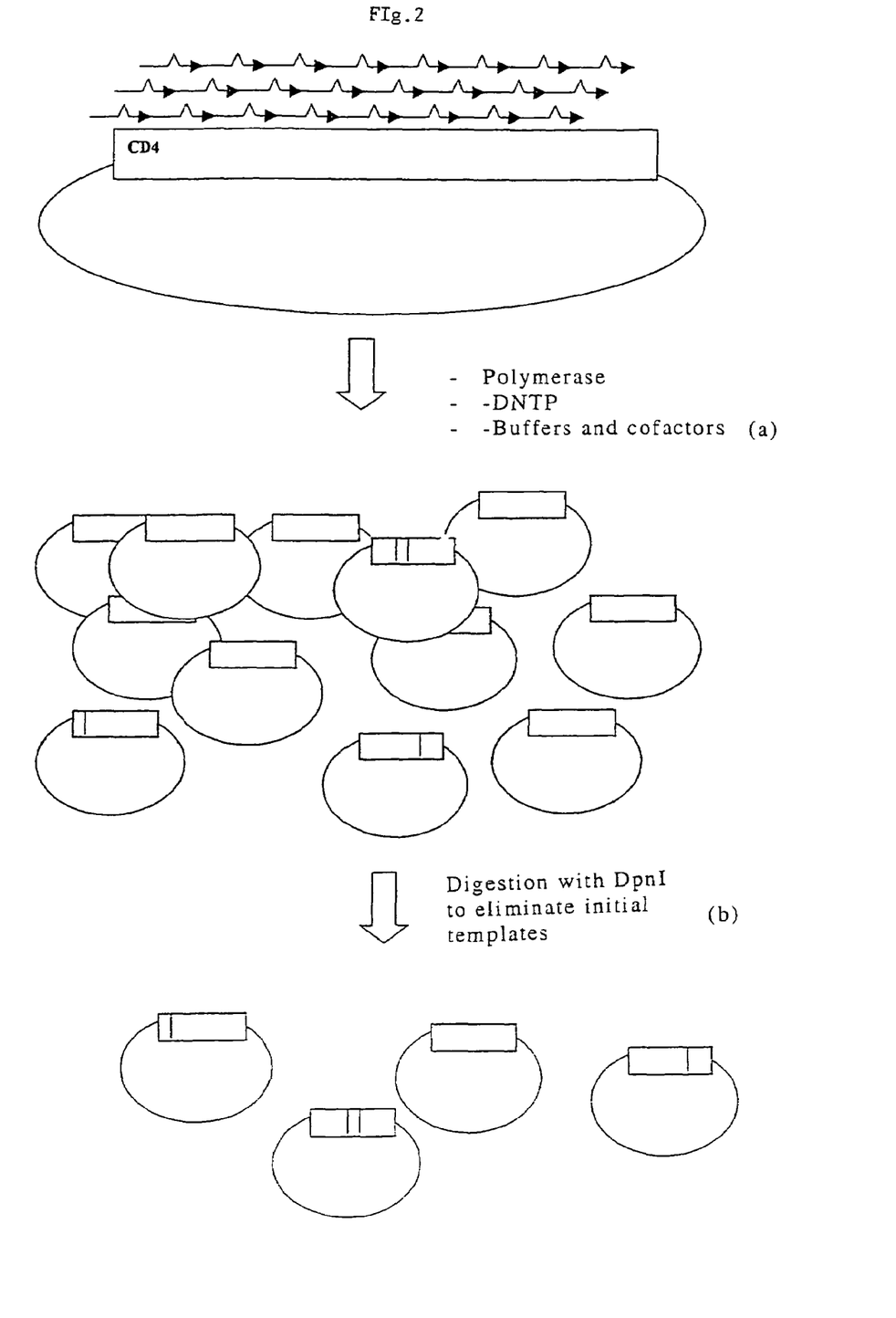
FIG. 2 is a diagram showing the steps of the mutagenesis process according to the invention from the mutant oligonucleotides in FIG. 1. The mutations in the DNA molecules are represented by a vertical line. The letters mean.
Figure 3:
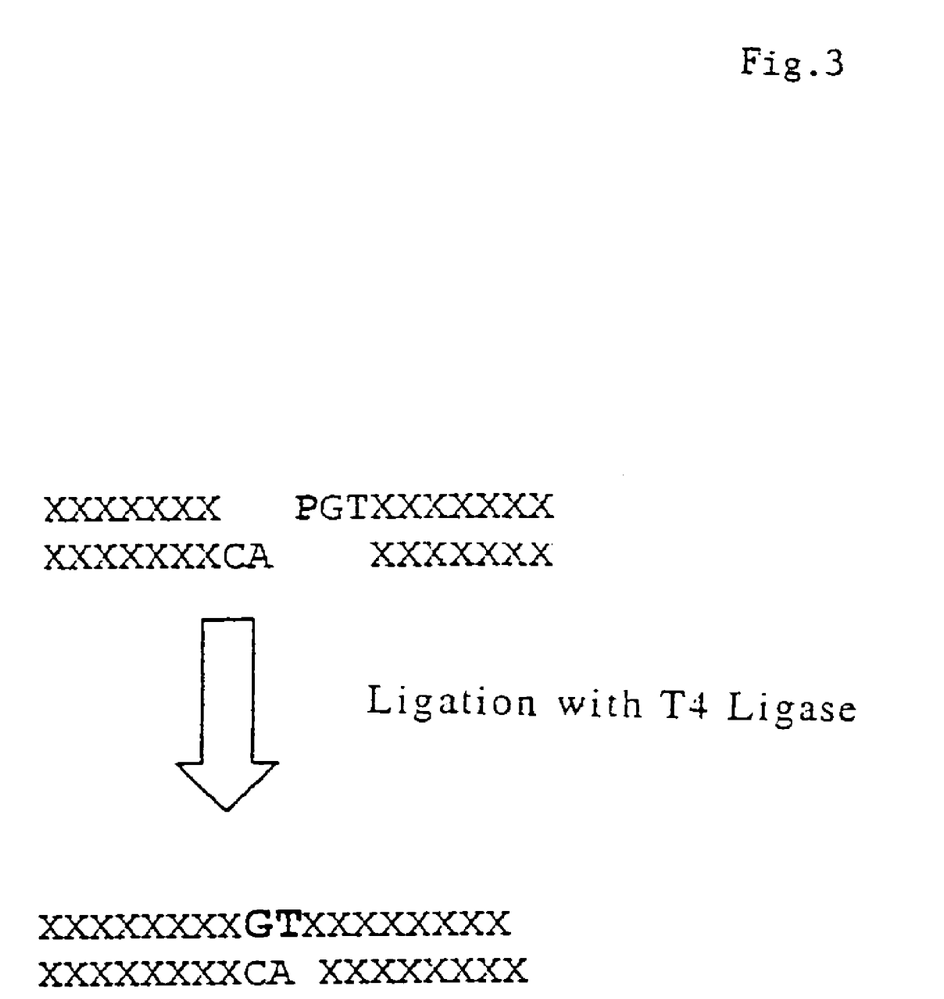
FIG. 3 shows an example of construction of mutant oligonucleotides from semi-oligonucleotides comprising ligation by T4 ligase.

A schematic diagram of the steps of the technique is given in FIG. 2.

At this stage, a statistical test on some DNA molecules from the library was carried out to measure the integration level of the mutations, i.e. the replacement of one of the 95 codons by an alanine codon. This test showed that the incorporation frequency for each oligonucleotide was close to 1%, which in this case was the desired value (1/N with N=95).

The mutant molecules were then amplified by bacterial culture and plasmid DNA preparation. Each of the plasmid DNA batches corresponding to a single type of mutant molecule was used to transfect eucaryote cells, and these cells were tested for conservation or loss of the epitopes carried by the CD4 molecule, whereby this activity was measured by anti-CD4 antibody binding.

EXAMPLE 2

Valine Scanning Using Reconstruction of the Oligonucleotides Reconstructed from Semi-Oligonucleotides A pool of 11 oligonucleotides were each reconstructed from two double-strand semi-oligonucleotides. The two semi-oligonucleotides were ligated by reaction with T4 ligase. Since only one of the two semi-oligonucleotides was phosphorylated at one of its 5' ends, this reaction resulted in forming a single complete oligonucleotide, comprising 18 bases (8 on each side were homologous, while the two median always were GT (FIG. 3).

These mutations, intended to replace the first two nucleotides of any codon, result in substituting a valine codon for each codon. As a matter of fact, because of the genetic code degenerescence, the valine codons can be written as GTN, where N is any of the 4 bases.

These 11 reconstructed oligonucleotides were homologous to 11 different regions of the molecule CD4, but carried the same mutation (change into valine) and were orientated in the same direction. The further procedure was the same as in example 1.

A mean incorporation frequency of the mutant oligonucleotides of about 9% (1/11) was sought in this example.

EXAMPLE 3

Improvement of an Active Site by Saturation Massive Mutagenesis

After the amino acids included in the active site of a protein have been determined, for example from massive mutagenesis data as shown in the previous examples, these amino acids can be subjected to saturation massive mutagenesis, i.e. introducing a large number of different codons to replace a particular codon. Thus 6 codons of the gene coding for the agaB protein, an enzyme involved in the synthesis of sugars, were identified as directly involved in this enzyme activity.

Figure 4:
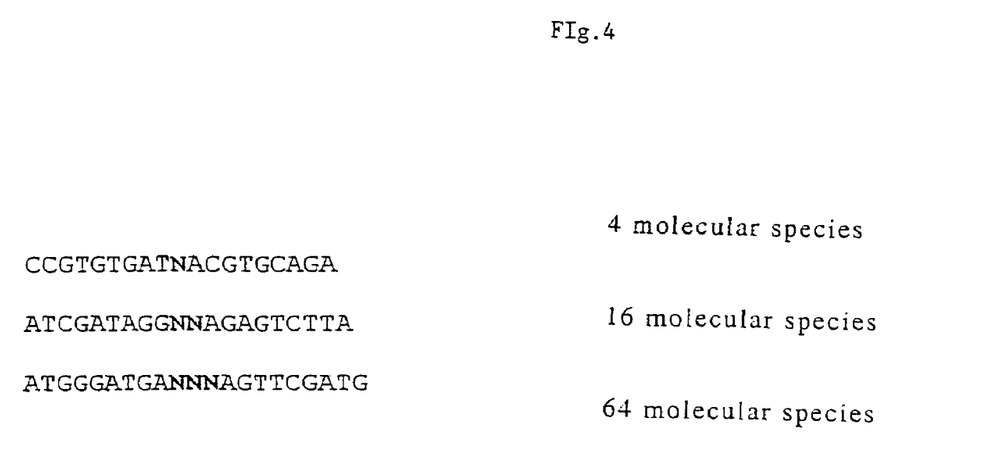
FIG. 4 gives examples of schematic representation of oligonucleotides containing bases degenerated at the points of mutation. The letter N means that any of the four bases can be present in this position. The contemplated oligonucleotide thus comprises a mixture of $4^N$ molecular species. SEQ ID NO:1 relates to the described 4 molecular species, SEQ ID NO:2 relates to the described 16 molecular species and SEQ ID NO:3 relates to the described 64 molecular species.

Six oligonucleotides centred at these codons were synthesized. On each side they were homologous to 9 bases of the sequence. The first two nucleotides of the wild sequence codons to be mutated were replaced by NN (FIG. 4). In this way, each of the 6 codons could be replaced by specific different codons or other amino acids.

Once these oligonucleotides were obtained, the massive mutagenesis reaction was identical to what is described in example 1.

A mean incorporation frequency of the mutant oligonucleotides of about 17% (⅙) was sought in this example.

These molecules of plasmid DNA were intended to be screened in order to determine an increase in the enzyme activity.

While only using a reduced number of mutant oligonucleotides containing degenerated bases, this example shows the adaptability of the technique according to the invention to random mutagenesis (change of a codon into a large number of other codons) in pre-determined positions.

EXAMPLE 4

Optimization of the Codons of a Gene

Genes generally contain codons which do not favour the expression of the proteins which they encode. These unfavourable codons can be seen as a mechanism for regulation of the gene expression. These unfavourable codons are rather well identified and it may be necessary to modify them into a codon more favourable to the expression of the protein without changing any amino acid.

Generally about 5% of the codons of a gene are unfavourable and limit the expression level of the corresponding protein. By modifying these codons, better expression levels of the gene during in vitro production of the corresponding protein could be obtained.

However, simultaneous modification of all the codons does not allow to obtain this expression improvement, probably due to the general sequence destabilization by too many modifications.

The best expression levels are most often obtained when just a few of the unfavourable codons are modified.

In this case, a library of mutations covering these unfavourable codons can be prepared using the technique of the invention, and the mutant molecules presenting the best expression levels are then selected. For each unfavourable codon, a mutant oligonucleotide must be synthesized with the mutations carried by these oligonucleotides being such that they change an unfavourable codon into a favourable codon, without changing the primary sequence of the corresponding protein.

In this context the mean incorporation frequency of the mutant oligonucleotides can be sought in a relatively wide range, for example between 1 and 20%. However, the number of simultaneous mutations, which allows to obtain the best expression levels, is not known. In this context, several libraries corresponding to different incorporation frequencies can be prepared. In order to prepare these libraries with different mutation levels, either the described process can be carried out using variable concentrations of oligonucleotides or the massive mutagenesis process can be carried out several times, i.e. using the library of mutants produced in a first massive mutagenesis as the template for a second massive mutagenesis.

The process is similar to what is presented in example 1. The mutant molecules are then screened depending on their expression level, i.e. the molecules with the best expression levels are selected.

---

The invention claimed is:

1. Process for mutagenesis of a target gene which comprises preparing a pool of N oligonucleotides overlapping or not with a sequence substantially complementary to at least one region of the target gene, then reacting said pool of oligonucleotides with said target gene under conditions allowing production of copies of the target gene carrying at least one mutation, wherein the target gene is carried by a double-strand circular plasmid, each oligonucleotide has a sequence complementary to a different region of the target gene and at least one mutation at the centre of the oligonucleotide sequence, the whole of said N oligonucleotides of the pool, with N higher than 5, covering all or part of the sequence of said target gene, and said pool of oligonucleotides is reacted with the target gene in the presence of a polymerase so as to generate a library of mutated genes where each mutation derived from a different oligonucleotide is present on average in less than 1/5 of the genes in the library.

2. Process of mutagenesis of a library of mutated target genes, which comprises preparing a pool of N oligonucleotides with a sequence substantially complementary to at least one region of the target mutated genes, then reacting said pool of oligonucleotides with said target mutated genes under conditions allowing the production of copies of the mutated target genes carrying at least one mutation, characterized in that the target mutated genes are carried by double-strand circular plasmids, each oligonucleotide has a sequence complementary to a different region of the target mutated genes and at least one mutation in the centre of the sequence of the oligonucleotide, the whole of said N oligonucleotides of the pool, with N higher than 5, covering all or part of the sequence of said target mutated genes, and said pool of oligonucleotides is reacted with the target mutated genes in the presence of a polymerase so as to generate a library of mutated genes where each mutation derived from a different oligonucleotide is present on average in less than 1/5 of the genes in the library.

3. Process of mutagenesis according to claim 1 characterized in that N is between about 5 and $10^6$, and each mutation derived from a different oligonucleotide is present on average in between 1/5 and $1/10^6$ of the genes in the library.

4. Process of mutagenesis according to claim 1, characterized in that the pool of oligonucleotides comprises N different oligonucleotides and each mutation derived from a different oligonucleotide is present on average in about 1/N of the genes in the library.

5. Process of mutagenesis according to claim 1 or claim 2, characterized in that the pool of oligonucleotides is reacted with the target gene of claim 1 or the library of target mutated genes of claim 2 with a molar ratio of each oligonucleotide to the target gene or the library of target mutated genes of between 0.01 and 100.

6. Process of mutagenesis according to claim 1 or claim 2, characterized in that the pool of oligonucleotides is reacted with the target gene of claim 1 or the library of target mutated genes of claim 2 in the presence of a polymerase having a strand displacement activity or an exonuclease 3'→5' activity.

7. Process of mutagenesis according to claim 6, characterized in that the pool of oligonucleotides is reacted with the target gene or the library of the target mutated genes in the presence of a polymerase having a strand displacement activity or an exonuclease 3'→5' activity and a ligase.

8. Process of mutagenesis according to claim 1, characterized in that the pool of oligonucleotides is reacted with the target gene or the library of target mutated genes in the presence of a polymerase having no strand displacement activity or exonuclease 3'→5' activity, and in the absence of ligase.

9. Process of mutagenesis according to claim 1 characterized in that the oligonucleotides of the pool have a size between 10 and 100 nucleotides.

10. Process of mutagenesis according to claim 1, characterized in that each oligonucleotide comprises one or more mutations at the centre of its sequence.

11. Process of mutagenesis according to claim 1, characterized in that the mutations of each oligonucleotide are selected from deletions and/or insertions of one or more nucleotides.

12. Process of mutagenesis according to claim 1; characterized in that each oligonucleotide in the pool is present in several copies, each copy having a different nucleotide at the site of said mutation or mutations.

13. Process of mutagenesis according to claim 1, characterized in that each mutation allows to introduce into each oligonucleotide the same codon or a codon corresponding to the same amino acid, as substituted for the original codon of the target gene.

14. Process of mutagenesis according to claim 13, characterized in that said same codon or a codon corresponding to the same amino acid corresponds to an amino acid selected from the group consisting of Ala, Val, Gly, Leu, and lie.

15. Process of mutagenesis according to claim 1, characterized in that it comprises the following steps:
   a) a template is prepared consisting of a plasmid containing the target gene and a resistance gene,
   b) an equimolar pool of oligonucleotides with a sequence complementary to a different region of the target gene and at least one mutation in the centre of the oligonucleotide is prepared, wherein the whole set of the oligonucleotides in the pool covering all or part of the sequence of said target gene,
   c) the pool of oligonucleotides prepared in step (b) is mixed with the plasmid from step (a) in a molar ratio of each oligonucleotide to the plasmid of between 0.01 and 100,
   d) the mixture from step (c) is denatured by heating to give a single-strand template,
   e) the mixture from step (d) is subjected to a temperature allowing hybridization of oligonucleotides to the template,
   f) at least one polymerase, its buffer and its co-factors and a sufficient amount of each of the triphosphate nucleotides to allow replication of the strands of the template from any of the oligonucleotides are added to the mixture,
   g) optionally, steps (d), (e) and (f) are repeated,
   h) those products of steps (f) or (g) which have been replicated are selected by any appropriate means,
   i) competent bacteria are transformed with the products selected in step (h) and the products comprising a plasmid are selected on a selective medium corresponding to the resistance gene carried by the plasmid from step (a).

16. Process of mutagenesis according to claim 15, characterized in that step (h) further comprises subjecting the products from step (f) to the action of a restriction enzyme thereby selecting the products which have been replicated.

17. Process of mutagenesis according to claim 16, characterized in that the restriction enzyme is DpnI.

18. Process of mutagenesis according to claim 15, characterized in that the oligonucleotides are phosphorylated at their 5' end, and in step (f), a ligase is added.

19. Process of mutagenesis according to claim 1, characterized in that the target gene is a molecule of nucleic acid coding for a protein of interest with or without its own regulation sequences.

20. Process of mutagenesis of a target protein or a library of target mutated proteins, characterized in that it comprises preparation of an expression library of mutated genes from a target gene coding for said protein according to claim 1, and said mutated genes are then expressed to produce a library of mutated genes, and said mutated proteins are optionally screened for a desired function.

21. Process of selection of mutated proteins presenting a modified action compared with the non-mutated proteins, or of mutated genes corresponding to said mutated proteins, characterized in that it comprises a process of mutagenesis according to claim 20, after screening of the mutated proteins for a desired function, the mutated proteins presenting said desired function are selected, and optionally the mutated genes corresponding to said mutated proteins are sequenced.

22. Process of mutagenesis of a target protein or a library of target mutated proteins according to claim 20, characterized in that it comprises the preparation of an expression library of mutated genes from a target gene coding for said protein according to the following steps:
   a) a template is prepared consisting of a plasmid containing the target gene or the library of target mutated genes and a resistance gene,
   b) an equimolar pool of oligonucleotides with a sequence complementary to a different region of the target gene or the library of target mutated genes and at least one mutation in the centre of the oligonucleotide is prepared, wherein the whole set of the oligonucleotides in the pool covering all or part of the sequence of said target gene,
   c) the pool of oligonucleotides prepared in step (b) is mixed with the plasmid from step (a) in a molar ratio of each oligonucleotide to the plasmid of between 0.01 and 100,
   d) the mixture from step (c) is denatured by heating to give a single-strand template,
   e) the mixture from step (d) is subjected to a temperature allowing hybridization of oligonucleotides to the template,
   f) at least one polymerase, its buffer and its co-factors and a sufficient amount of each of the triphosphate nucleotides to allow replication of the strands of the template from any of the oligonucleotides are added to the mixture,
   g) optionally, steps (d), (e) and (f) are repeated,
   h) those products of steps (f) or (g) which have been replicated are selected by any appropriate means,
   i) competent bacteria are transformed with the products selected in step (h) and the products comprising a plasmid are selected on a selective medium corresponding to the resistance gene carried by the plasmid from step (a)
   j) the selective medium is incubated at an appropriate temperature for sufficient time for individual bacterial colonies to grow,
   k) individual cultures of bacteria from the colonies in step (j) are inoculated,
   l) samples of plasmid DNA are prepared from the cultures of step (k),
   m) the biological activity associated with each sample of plasmid DNA from step (l) is measured and the result is compared with that obtained using non-mutated plasmid DNA.
   n) optionally the plasmid DNA samples which showed significant modifications of biological activity are sequenced.

23. Process of mutagenesis according to claim 6, wherein the polymerase having a strand displacement activity is the Taq polymerase.

24. Process of mutagenesis according to claim 6 or claim 23, wherein the polymerase having an exonuclease 3'→5' activity is the Pfu polymerase.

25. Process of mutagenesis according to claim 15, wherein the added ligase is a heat stable ligase.

26. Process of mutagenesis of a target protein or a library of target mutated proteins according to claim 20, wherein said mutated protein are optionally screened for a desired function in relation to the target protein.

27. Process of mutagenesis according to claim 2, characterized in that it comprises the following steps:
   a) a template is prepared consisting of a plasmid containing the library of target mutated genes and a resistance gene,
   b) an equimolar pool of oligonucleotides with a sequence complementary to a different region of the library of target mutated genes and at least one mutation in the centre of the oligonucleotide is prepared, wherein the whole set of the oligonucleotides in the pool covering all or part of the sequence of said target gene,
   c) the pool of oligonucleotides prepared in step (b) is mixed with the plasmid from step (a) in a molar ratio of each oligonucleotide to the plasmid of between 0.01 and 100,
   d) the mixture from step (c) is denatured by heating to give a single-strand template,
   e) the mixture from step (d) is subjected to a temperature allowing hybridization of oligonucleotides to the template,
   f) at least one polymerase, its buffer and its co-factors and a sufficient amount of each of the triphosphate nucleotides to allow replication of the strands of the template from any of the oligonucleotides are added to the mixture,
   g) optionally, steps (d), (e) and (f) are repeated,
   h) those products of steps (f) or (g) which have been replicated are selected by any appropriate means,
   i) competent bacteria are transformed with the products selected in step (h) and the products comprising a plasmid are selected on a selective medium corresponding to the resistance gene carried by the plasmid from step (a).

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: 4 molecular
      species
<220> FEATURE:
<221> NAME/KEY: misc_feature
<222> LOCATION: (10)
<223> OTHER INFORMATION: n is any base

<400> SEQUENCE: 1
ccgtgtgatn acgtgcaga                                                19

<210> SEQ ID NO 2
<211> LENGTH: 20
<212> TYPE: DNA
<213> ORGANISM: Artificial Sequence
<220> FEATURE:
```

-continued

```
<223> OTHER INFORMATION: Description of Artificial Sequence: 16
      molecular species
<220> FEATURE:
<221> NAME/KEY: misc_feature
<222> LOCATION: (10)..(11)
<223> OTHER INFORMATION: n is any base

<400> SEQUENCE: 2
atcgataggn nagagtctta                                           20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: 64
      molecular species
<220> FEATURE:
<221> NAME/KEY: misc_feature
<222> LOCATION: (10)..(12)
<223> OTHER INFORMATION: n is any base

<400> SEQUENCE: 3
atgggatgan nnagttcgat g                                         21
```